US006296608B1

(12) United States Patent
Daniels et al.

(10) Patent No.: US 6,296,608 B1
(45) Date of Patent: *Oct. 2, 2001

(54) DIAGNOSING AND PERFORMING INTERVENTIONAL PROCEDURES ON TISSUE IN VIVO

(75) Inventors: Douglas J. Daniels, Mendon; Michael S. Banik, Bolton, both of MA (US)

(73) Assignee: Boston Scientific Corporation, Natick, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/679,425

(22) Filed: Jul. 8, 1996

(51) Int. Cl.[7] .............................. A61B 1/012; A61B 1/06; A61B 6/00
(52) U.S. Cl. ...................... 600/104; 600/113; 600/182; 600/478
(58) Field of Search ................................. 600/104, 476, 600/478, 473, 475, 477, 564

(56) References Cited

U.S. PATENT DOCUMENTS

| | | |
|---|---|---|
| 4,211,229 | 7/1980 | Wurster . |
| 4,675,529 * | 6/1987 | Kushida ........................... 600/478 |
| 4,768,513 * | 9/1988 | Suzuki ............................. 600/476 |
| 4,807,593 * | 2/1989 | Ito .................................. 600/114 |
| 4,981,138 * | 1/1991 | Deckelbaum et al. ............ 600/478 |
| 5,078,150 * | 1/1992 | Hara et al. ........................ 600/478 |
| 5,122,147 | 6/1992 | Sewell, Jr. . |
| 5,174,297 | 12/1992 | Daikuzono . |
| 5,197,470 | 3/1993 | Helfer et al. . |

(List continued on next page.)

FOREIGN PATENT DOCUMENTS

| | | | |
|---|---|---|---|
| 39 20 706 * | 1/1991 | (DE) | ................................... 600/182 |
| 0 248 761 A | 12/1987 | (EP) . | |
| 0 573 264 A | 12/1993 | (EP) . | |
| 90 13260 | 11/1990 | (WO) . | |
| 94 10920 | 5/1994 | (WO) . | |
| 94 11771 | 5/1994 | (WO) . | |

OTHER PUBLICATIONS

"Spectrascience Received 510(K) Premarket Notification Clearance from United States Food and Trust Administration for FiberopticBiopsy Forceps," First! An Information Service of Individual, Inc., p. 5 (Dec. 16, 1996 at 08:56 EST, Bustiness Wire, File: b1216085.600).

Primary Examiner—John P. Leubecker
(74) Attorney, Agent, or Firm—Testa, Hurwitz & Thibault, LLP (57) ABSTRACT

A catheter for diagnosing and performing an interventional procedure on tissue has an elongated catheter shaft, and optical fibers, extending through the catheter shaft, for transmitting light to tissue located at a distal end of the catheter and conveying light back from the tissue for analysis by a spectroscopic diagnosis system to determine whether an interventional procedure should be performed on the tissue. An interventional device is located at the distal end of the catheter for engaging tissue diagnosed by the spectroscopic diagnosis system in order to perform the interventional procedure on the tissue. An assembly for imaging and performing an interventional procedure on tissue has an endo scope in combination with an endoscopically insertable catheter having an ultrasound imaging device for imaging a tissue structure located at a distal end of the endoscope so as to enable the depth of penetration of the tissue structure to be displayed, and an endoscopically insertable interventional device for engaging the tissue structure imaged by the ultrasound imaging device.

32 Claims, 5 Drawing Sheets

U.S. PATENT DOCUMENTS

| | | | |
|---|---|---|---|
| 5,261,889 | * | 11/1993 | Laine et al. .............................. 600/104 |
| 5,280,788 | * | 1/1994 | Janes et al. ............................ 600/476 |
| 5,290,276 | * | 3/1994 | Sewell, Jr. ............................. 600/114 |
| 5,350,375 | | 9/1994 | Deckelbaum et al. . |
| 5,382,163 | | 1/1995 | Putnam . |
| 5,419,323 | | 5/1995 | Kittrell et al. . |
| 5,601,087 | * | 2/1997 | Gunderson et al. ................. 600/478 |
| 5,632,740 | | 5/1997 | Koch et al. . |
| 5,701,902 | | 12/1997 | Vari et al. . |
| 5,749,830 | * | 5/1998 | Kaneko et al. ....................... 600/476 |
| 5,749,889 | * | 5/1998 | Bacich et al. ......................... 600/104 |
| 5,762,613 | * | 6/1998 | Sutton et al. .......................... 600/564 |
| 5,785,658 | * | 7/1998 | Benaron et al. ...................... 600/476 |
| 5,843,000 | * | 12/1998 | Nishioka et al. ..................... 600/104 |

\* cited by examiner

DIAGNOSING AND PERFORMING INTERVENTIONAL PROCEDURES ON TISSUE IN VIVO

BACKGROUND OF THE INVENTION

This application relates to diagnosing and performing interventional procedures on tissue using endoscopically insertable catheters.

Lesions in body lumens such as the alimentary track may be diagnosed by inserting an endoscope into the alimentary track and inserting through a working channel of the endoscope a catheter having optical fibers for transmitting light to tissue located at a distal end of the catheter and for conveying light back from the tissue for analysis by a spectroscopic diagnosis system. If the spectroscopic diagnosis system determines an interventional procedure should be performed on the tissue, a biopsy of the tissue may be taken or the tissue may be otherwise removed or treated.

SUMMARY OF THE INVENTION

One aspect of the invention features a catheter for diagnosing and performing an interventional procedure on tissue. The catheter has an elongated catheter shaft, and optical fibers, extending through the catheter shaft, transmit light to tissue located at a distal end of the catheter shaft and convey light back from the tissue for analysis by a spectroscopic diagnosis system to determine whether an interventional procedure should be performed on the tissue. An interventional device is located at the distal end of the catheter shaft for engaging tissue diagnosed by the spectroscopic diagnosis system in order to perform the interventional procedure on the tissue.

In various embodiments the catheter is constructed to be inserted through the working channel of an endoscope, and the interventional device is, for example, a scalpel, forceps jaws, a snare, a scissors, or a needle. An interventional needle can be used, for example, to cut the tissue, to apply an adhesive material to the tissue, to inject a chemical ablation fluid into the tissue, or to inject a marking fluid into the tissue so as to enable the tissue to be treated by another interventional device, which may be located on another catheter. Because the interventional device is located on the same catheter as the optical fibers, the physician can perform the interventional procedure on the tissue without having to remove the catheter from the patient's body. Moreover, the diagnosis and interventional procedure can be accomplished at multiple sites without having to remove the catheter from the patient's body. In various embodiments the interventional device is, for example, a scalpel, forceps jaws, a snare, a scissors, or a needle.

Another aspect of the invention features an assembly comprising an endoscope, a catheter shaft insertable through a working channel of the endoscope having optical fibers for transmitting light to tissue and from tissue for analysis by a spectroscopic diagnosis system to determine whether an interventional procedure should be performed on the tissue, and an interventional device, insertable through a working channel of the endoscope, for performing the interventional procedure on the tissue.

Another aspect of the invention features a method for imaging and performing an interventional procedure on tissue. A catheter having an ultrasound imaging device located at its distal end is inserted through a working channel of an endoscope, for imaging a tissue structure located at a distal end of the endoscope, and the tissue structure is displayed in a manner that indicates-the depth of penetration of the tissue structure into the body of the living being. An interventional device, which is inserted through a working channel of the endoscope, performs interventional therapy on the tissue structure in a manner responsive to the displayed depth of penetration of the tissue structure.

This aspect of the invention enables the physician to determine the depth to which a tumor has grown into or through the wall of a lumen in order to determine whether the tumor can be removed safely from the lumen. The physician can rely on the ultrasound image display to determine how much tissue to remove in view of the depth of penetration of the tissue structure, and can also observe the ultrasound image of the tissue structure while performing the interventional procedure on the tissue structure so as to ensure that an appropriate amount of tissue is removed.

In general, the invention aids physicians in the accurate early diagnosis of patients with cancer or other abnormalities inside the body. Many cancers or other abnormalities can be treated efficiently if diagnosed and treated early enough in the least invasive manner. The invention helps physicians to locate suspect areas, diagnose accurately, and sample and treat tissue efficiently. The invention also provides high diagnostic accuracy and short procedural time by providing accurate data and avoiding unnecessary biopsies. Consequently, overall health care costs are low because of low lab analysis costs and minimal outpatient hospital visits.

Numerous other features, objects, and advantages of the invention will become apparent from the following detailed description when read in connection with the accompanying drawings.

DETAILED DESCRIPTION

FIGS. 1–6 refer to an endoscopically insertable catheter having optical fibers for transmitting light to tissue and for conveying light back from tissue for analysis by a spectroscopic diagnosis system and having a needle for performing an interventional procedure on the tissue, namely, injecting india ink into tissue diagnosed by the spectroscopic diagnosis system in order to mark the tissue for biopsy, treatment, or removal by another interventional device. If the spectroscopic diagnosis system determines that the tissue should be treated, the catheter having the optical fibers and needle is withdrawn from the endoscope and a catheter having forceps jaws is inserted through the endoscope in order to obtain a biopsy of the tissue or to remove or treat the tissue.

Figure 1:
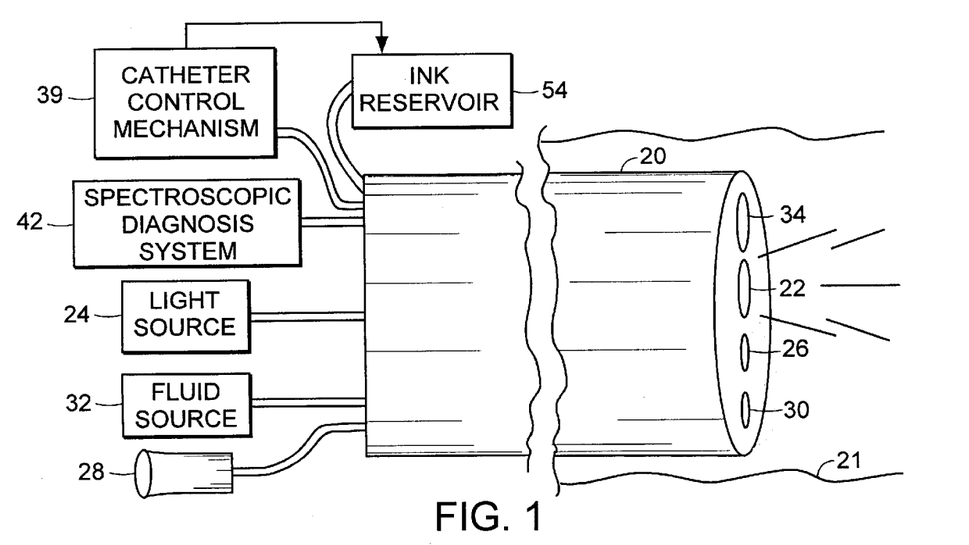
FIGS. 1–6 are a set of drawings showing the steps of a process for spectroscopically diagnosing and marking tissue using an endoscopically insertable catheter and for removing tissue using another endoscopically insertable catheter.

With reference to FIG. 1, a distal end of an endoscope 20 is inserted through a lumen 21 of a patient's body, such as the esophagus, rectum or pulmonary tract. Endoscope 20 has an optical fiber 22 connected to a light source 24 located at a proximal end of endoscope 20 for transmitting light to tissue located at the distal end of endoscope 20, an optical fiber 26 connected to an eyepiece 28 located at the proximal end of endoscope 20 for viewing the tissue, a fluid channel 30 connected to a fluid source 32 located at the proximal end of endoscope 20 for flushing the tissue with fluid such as a wash for the visual fiber optics, and a working channel 34 for receiving a catheter. In FIG. 1, light source 24 is turned on.

Figure 2:
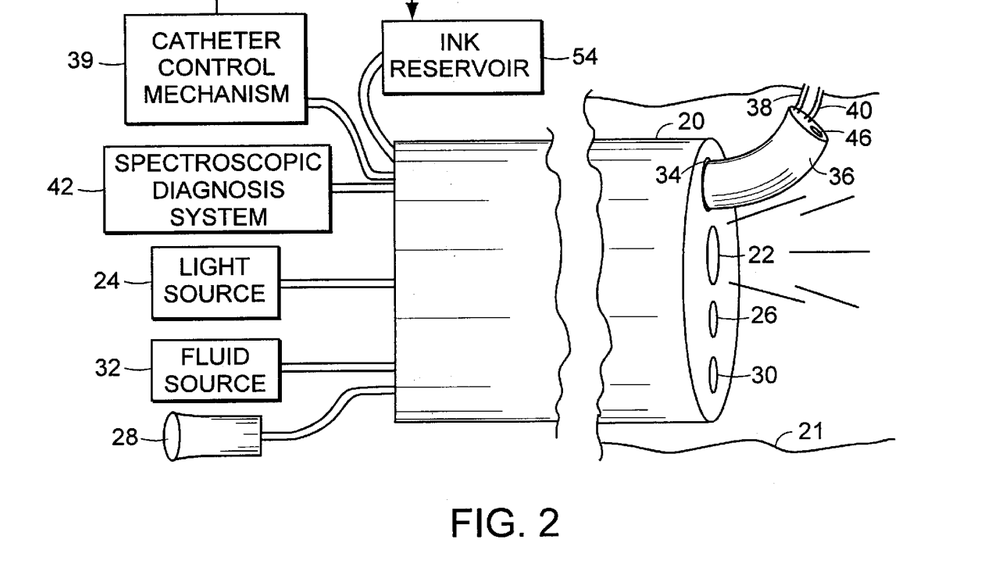

With reference to FIG. 2, a catheter 36 having an elongated catheter shaft is inserted through working channel 34 of endoscope 20. Catheter 36 has optical fibers 38 and 40, which extend through the catheter shaft and are connected to a spectroscopic diagnosis system 42 located at the proximal end of endoscope 20. Optical fibers 38 and 40 can be made of a quartz glass component or other suitable glass or polymer material capable of transmitting and receiving wavelengths necessary to distinguish between healthy and abnormal tissue that has been treated by a diagnostic reagent. The optical fibers may be bundled together as a single light transmission and reception probe rather than the two discrete fibers shown in FIGS. 2–3 the probe including an outer sheath made of SST or a suitable semi-rigid polymer that is non-reactive to diagnostic reagents. Catheter 36 is connected to a catheter control mechanism 39 located at the proximal end of endoscope 20 that controls the longitudinal movement of catheter 36 within working channel 34. Catheter control mechanism 39 also controls the longitudinal movement of optical fibers 38, 40 and may extend or retract optical fibers 38,40 with respect to catheter 36. In FIG. 2, light source 24 is turned on and optical fibers 38, 40 are extended from catheter 36 to the tissue.

Figure 3:
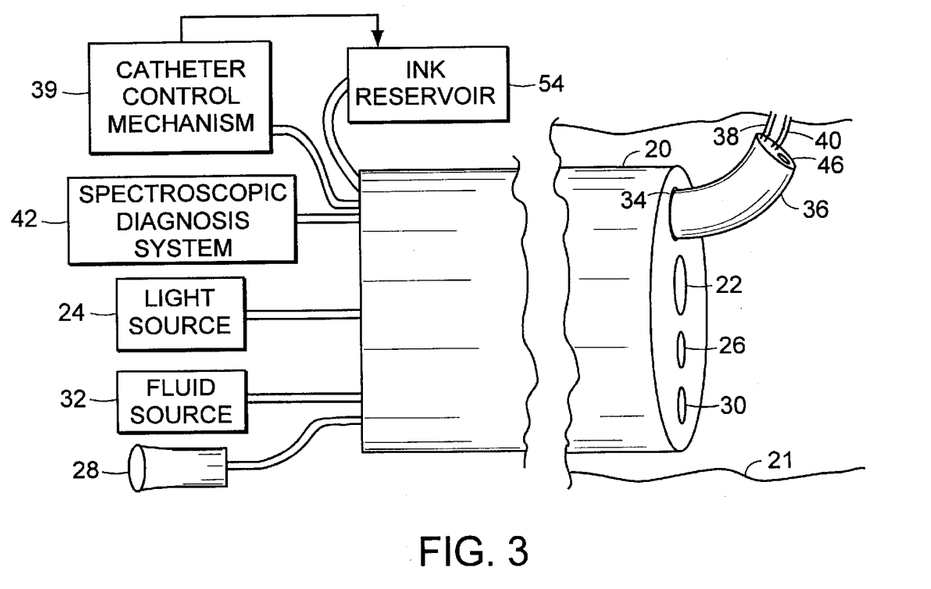

With reference to FIG. 3, light source 24 is turned off, optical fiber 38 transmits light to the tissue, and optical fiber 40 conveys light back from the tissue for analysis by spectroscopic diagnosis system 42 to determine whether the tissue should be treated.

For example, optical fiber 38 transmits a monochromatic light beam having a wavelength or set of wavelengths selected to cause the tissue to fluoresce in a manner such that at one wavelength of the fluorescent light the intensity is approximately the same regardless of whether the tissue is normal or cancerous and at another wavelength of the fluorescent light the intensity differs substantially depending on whether the tissue is normal or cancerous. By analyzing the ratio of the intensity of the fluorescent light at the wavelength at which the intensity is approximately the same regardless of whether the tissue is normal or cancerous to the intensity of the fluorescent light at the wavelength at which the intensity differs substantially depending whether the tissue is normal or cancerous, spectroscopic diagnosis system 42 can determine whether the tissue is normal or cancerous, and in some instances whether the tissue is a benign tumor. The tissue may first be treated by a diagnostic reagent that bonds more selectively with diseased (cancerous) tissue than with normal tissue, or vice versa, and that absorbs light transmitted through the catheter and thereby causes the tissue to fluoresce at a wavelength or set of wavelengths different from the transmission wavelength. The intensity of the light conveyed back to the spectroscopic diagnosis system may be displayed graphically through the aid of a computer as a function of wavelength, and the endoscopist can interpret the data.

Figure 4:
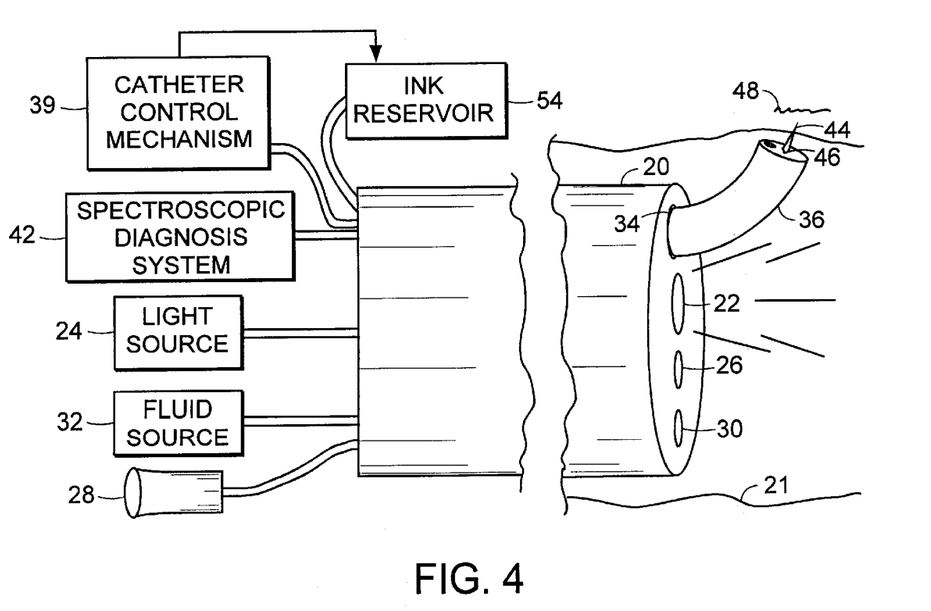

Referring to FIG. 4, if spectroscopic diagnosis system 42 determines that the tissue should be treated, catheter control mechanism 39 retracts optical fibers 38 and 40 into catheter 36, and light source 24 is turned on. Catheter control mechanism 39 also controls the longitudinal movement of a needle 44 which is located at the distal end of catheter 36 and extends needle 44 to the tissue. Needle 44, which can be made of SST or a suitable semirigid polymer that is non-reactive to diagnostic reagents, extends through a lumen 46 in the catheter shaft. Needle 44 and optical fibers 38 and 40 may be combined together as a single probe. Catheter control mechanism 39 causes india ink 48 from ink reservoir 54 to be injected through needle 44 into the tissue to be treated.

Optical fiber 38 transmits light to the tissue at a number of points and optical fiber 40 conveys light back from the tissue for analysis by spectroscopic diagnosis system 42 in order to determine whether the tissue is cancerous at each of these points. Each such point that is determined to be cancerous is marked by india ink 48 using needle 44.

Figure 5:
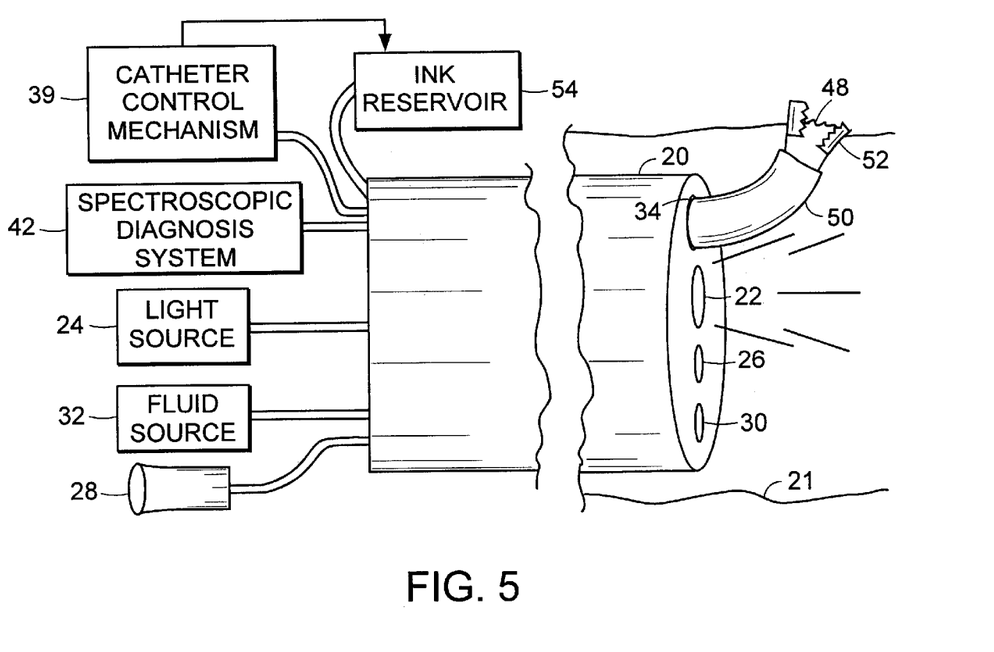

With reference to FIG. 5, light source 24 is turned on, and catheter 36 having optical fibers 38, 40 and needle 44 is withdrawn from working channel 34, and a catheter 50 having forceps jaws 52 located at its distal end is inserted through working channel 34. Forceps jaws 52 are used to remove the tissue diagnosed by the spectroscopic diagnosis system 42 and marked by india ink 48.

Numerous other embodiments are also within the scope of the claims. For example, FIGS. 6–10 are drawings of different embodiments of an endoscopically insertable catheter 100 combining optical fibers and various other types of interventional devices. Catheter 100 can be inserted in an endoscope as shown in FIGS. 1–5 in order to perform spectroscopic diagnosis on tissue and remove cancerous tissue without having to mark the cancerous tissue with india ink. After the interventional device removes the cancerous tissue, the optical fibers are used to perform spectroscopic diagnosis on the remaining tissue to determine whether all of the cancerous tissue has been removed.

Figures 6, 7:
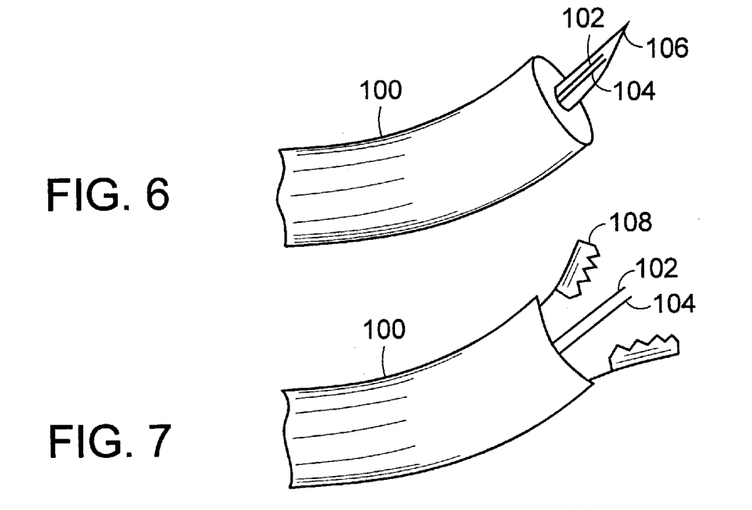
FIG. 7 is a drawing of an endoscopically insertable catheter combining optical fibers and forceps jaws.

In FIG. 6, catheter 100 has optical fibers 102, 104 glued to a surface of a scalpel 106.

In FIG. 7, catheter 100 has optical fibers 102, 104 placed between forceps jaws 108, which may be multiple sampling biopsy forceps jaws capable of removing multiple samples of tissue into the body of catheter 100 as described in U.S. patent application Ser. No. 08/193,382, the entire disclosure of which is hereby incorporated herein by reference. The forceps jaws are caused to open up as shown in FIG. 7 by the withdrawal of an outer sleeve of the catheter (not shown) in the proximal direction and are caused to close together by pushing the outer sleeve in the distal direction. There is a hole at the tip of the forceps jaws through which the optical fibers can extend, the optical fibers being extendable and retractable with respect to the catheter and with respect to the forceps jaws. The forceps jaws can be used to remove tissue known to be unhealthy or to obtain biopsy samples for additional, cellular analysis. The optical fibers are of course retracted when the forceps jaws are being used. If the forceps jaws are of the multiple-biopsy type, the optical fibers can be bundled together as a single probe designed to spear through the biopsy samples within the catheter for continued diagnosis at additional sites.

Figure 8:
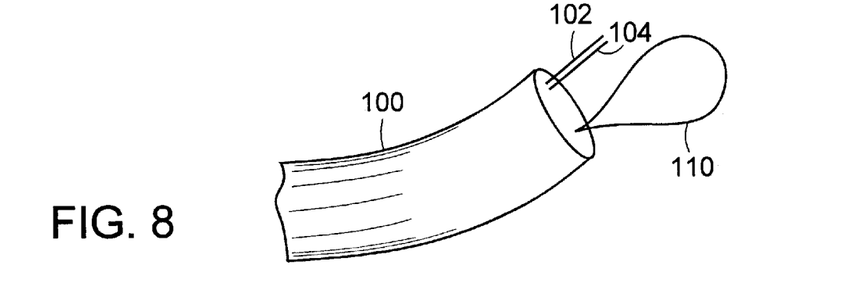
FIG. 8. is a drawing of an endoscopically insertable catheter combining optical fibers and a polypectomy snare.

Referring to FIG. 8, catheter 100 has optical fibers 102, 104 placed next to a polypectomy snare 110, which can be looped around a polyp and quickly retracted into catheter 100 to excise the polyp. The optical fibers may alternatively pass through the same lumen as the snare.

Figure 9:
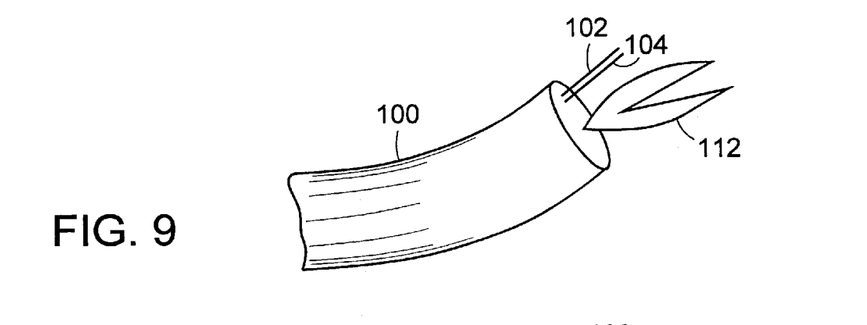
FIG. 9 is a drawing of an endoscopically insertable catheter combining optical fibers and scissors.

Referring to FIG. 9, catheter 100 has optical fibers 102, 104 placed next to scissors 112. Alternatively, the optical fibers may be glued to one of the scissors blades.

Figure 10:
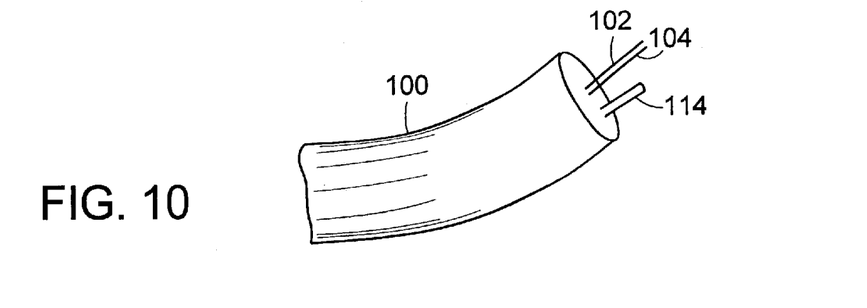
FIG. 10 is a drawing of an endoscopically insertable catheter combining optical fibers and a needle.

In FIG. 10, catheter 100 has optical fibers 102, 104 placed next to a needle 114, similar in construction to needle 44 described above in connection with FIGS. 1–5. Needle 114 may be constructed to inject chemical ablation fluid or other drugs into tissue, possibly including time-release capsules containing cancer-fighting substances, to cut tissue, or to apply glue for temporarily adhering tissue between the esophagus and the stomach for treating gastroesophageal reflux disease. Localized chemical ablation or drug treatment can be performed at high concentration because of the specificity with which spectroscopic diagnosis can identify the location of unhealthy tissue. Needle 114 of FIG. 10 or needle 44 of FIGS. 1–5 can also be used to inject a diagnostic reagent into a suspect site that bonds more selectively with diseased (cancerous) tissue than with normal tissue, or vice versa, as described above. Such a needle for injection of a diagnostic reagent can also be included in any of the catheters of FIGS. 6–9. In each of the embodiments of FIGS. 6–10, optical fibers 102, 104 are extendable and retractable with respect to catheter 100, and with the exception of the embodiment of FIG. 6, in which the optical fibers are glued to scalpel 106, any movement capabilities of optical fibers 102, 104 on the one hand and the interventional device on the other hand can be completely independent of each other.

Each of the embodiments described above in connection with FIGS. 1–10 can be modified by eliminating the endoscope and adding additional optical fibers to the catheter for use in connection with the imaging function, or by using one or more optical fibers of the catheter not only in connection with the spectroscopic diagnosis function but also in connection with the imaging function. Since the catheter would be used without an endoscope, the catheter would have a steerable tip to allow movement and positioning of the catheter. The lumen of the catheter needle, in embodiments having such a needle, can double as a wash for the visual fiber optics as well as a vacuum and air source. One advantage of such a construction is that the catheter would not have to be as large as an endoscope combined with a catheter, because no endoscope working channel is required.

Figure 11:
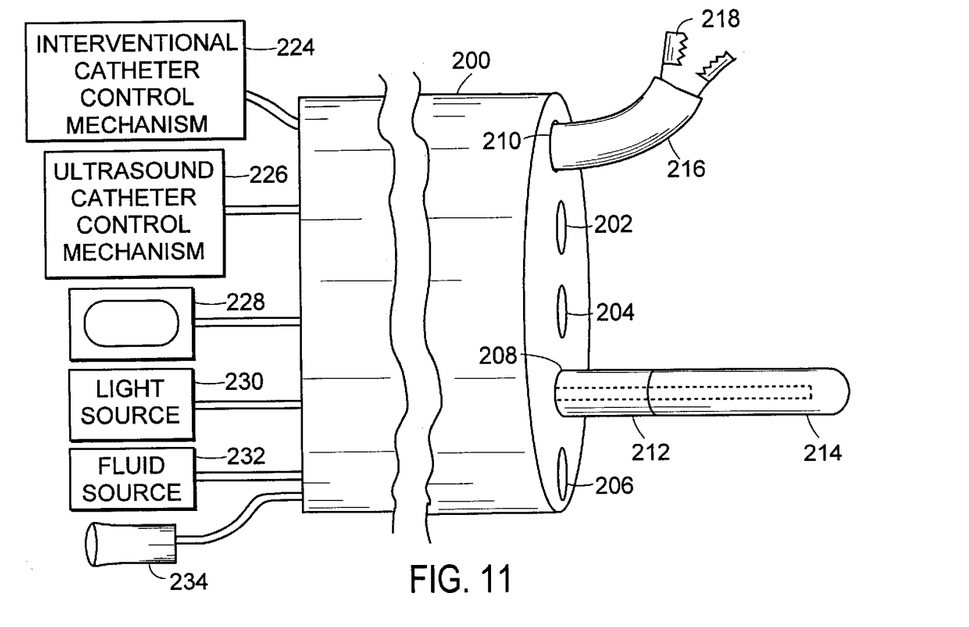
FIG. 11 is a drawing of an endoscope in combination with an endoscopically insertable catheter having forceps jaws and an endoscopically insertable catheter having an ultrasound imaging device.

With reference to FIG. 11, an endoscope 200 is combined with an endoscopically insertable catheter 216 having forceps jaws 218 and an endoscopically insertable catheter 212 having a rotatable ultrasound imaging transducer 214. Ultrasound imaging transducer 214 provides a visual image of the tumor, which can be useful in determining the depth to which a tumor has grown into or through the wall of a lumen in order to determine whether the tumor can be removed safely from the lumen. If the tissue structure imaged by ultrasound imaging transducer 214 can be removed safely from the lumen, forceps jaws 218 are used to remove the tissue structure. The visual image can also be used to determine how much tissue should be removed. The imaging can be performed simultaneously with the tissue removal, so as to enable the physician to see whether the tissue structure has been completely removed.

Endoscope 200 has an optical fiber 202 for transmitting light from light source 230 to tissue located at a distal end of endoscope 200, an optical fiber 204 for conveying light back from the tissue to eyepiece 234 for viewing tissue, a fluid channel 206 for flushing tissue with fluid provided by fluid source 232, and working channels 208, 210 for receiving catheters 212 and 216 respectively. Interventional catheter control mechanism 224 controls the longitudinal movement of catheter 216 within working channel 210 as well as the operation of forceps jaws 218.

Similarly, ultrasound catheter control mechanism 226 controls the longitudinal movement of ultrasound catheter 212 within working channel 208 as well as the operation of ultrasound transducer 214, including its rotation, transmission of ultrasound pulses, and detection of reflected pulses by the transducer. The ultrasound image of the tissue imaged by the ultrasound transducer is displayed by ultrasound image display 228.

The endoscope of FIG. 11 also may be used in combination with any of the different endoscopically insertable catheters combining optical fibers and interventional devices described above and shown in FIGS. 6–10, which may be substituted for interventional catheter 216.

Figure 12:
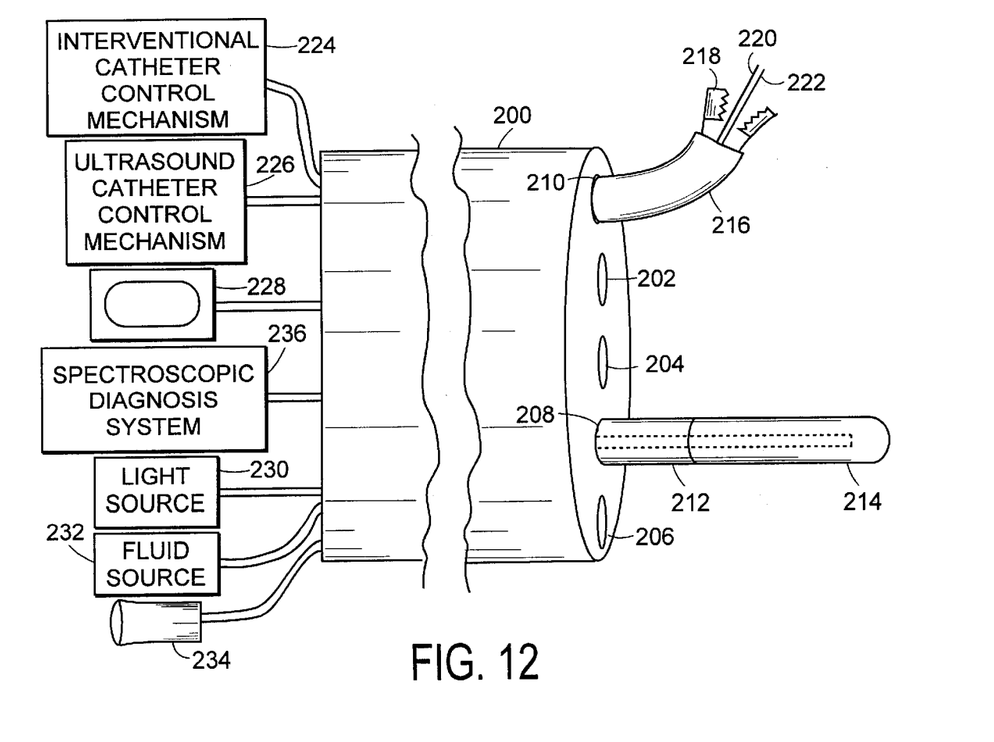
FIG. 12 is a drawing of an endoscope in combination with an endoscopically insertable catheter having optical fibers and forceps jaws and an endoscopically insertable catheter having an ultrasound imaging device.

For example, in FIG. 12, catheter 216 has forceps jaws 218 and optical fibers 220, 222, which are connected to a spectroscopic diagnosis system 236 that spectroscopically diagnoses the tissue to determine whether the tissue should be treated, as is described above in connection with FIG. 7.

If the tissue is found to be cancerous or otherwise in need of removal, ultrasound imaging catheter 214 is used to measure the depth to which a tumor has grown into or through the wall of a lumen to determine whether the tumor can be removed safely from the lumen. If the cancerous tissue imaged by ultrasound imaging device 214 can be removed safely from the lumen, forceps jaws 218 are used to remove the cancerous tissue. After forceps jaws 218 remove the cancerous tissue, optical fibers 220, 222 are used to perform spectroscopic diagnosis on the tissue to determine whether all of the cancerous tissue has been removed.

There have been described novel and improved apparatus and techniques for diagnosing and performing interventional procedures on tissue. It is evident that those skilled in the art may now make numerous uses and modifications of and departures from the specific embodiments described herein without departing from the inventive concept. For example, other interventional devices may be substituted for the ones described above and set forth in the drawings.

What is claimed is:

1. A catheter, comprising:
    an elongated catheter shaft defining at least two lumens and including a distal end;
    a first optical fiber, removably insertable into one of the at least two lumens of the catheter shaft and extendable beyond the distal end of the catheter shaft, for transmitting light to tissue located at a distal end of the catheter shaft;
    a second optical fiber, removably insertable into one of the at least two lumens of the catheter shaft and extendable beyond the distal end of the catheter shaft, for conveying light back from the tissue for analysis by a spectroscopic diagnosis system to determine whether an interventional procedure should be performed on the tissue, wherein said second optical fiber and said first optical fiber are discrete fibers and at least one of the fibers includes a viewing device for converting a second conveyed light back from the tissue into a visual observation image of the tissue; and
    an interventional device located at the distal end of the catheter shaft for engaging tissue diagnosed by the spectroscopic diagnosis system in order to perform the interventional procedure on the tissue, wherein said interventional device is physically separable from said first and second optical fibers.

2. The catheter of claim 1, wherein the interventional device comprises a scalpel.

3. The catheter of claim 1, wherein the interventional device comprises forceps jaws.

4. The catheter of claim 1, wherein the interventional device comprises a snare.

5. The catheter of claim 1, wherein the interventional device comprises a scissors.

6. The catheter of claim 1, wherein the interventional device comprises a needle.

7. The catheter of claim 6, wherein the needle is constructed to inject a marking fluid into the tissue.

8. The catheter of claim 6, wherein the needle is constructed to inject a chemical ablation fluid into the tissue.

9. The catheter of claim 6, wherein the needle is constructed to cut the tissue.

10. The catheter of claim 6, wherein the needle is constructed to apply an adhesive material to the tissue.

11. The catheter of claim 6, wherein the needle is constructed to convey a fluid to the tissue useful for enabling visual observation of the tissue.

12. The catheter of claim 6, wherein the needle is constructed to apply a vacuum to the tissue.

13. The catheter of claim 1, wherein the catheter shaft is constructed to be inserted through the working channel of an endoscope.

14. The catheter of claim 1, wherein at least one of the optical fibers is further constructed for conveying visualization light to the tissue.

15. A method of diagnosing and performing an interventional procedure on tissue, comprising the steps of:

inserting into a lumen of a body of a living being a catheter having an elongated shaft defining at least two lumens and including a distal end, a first optical fiber, removably insertable into one of the at least two lumens of the catheter shaft and extendable beyond the distal end of the catheter shaft, for transmitting light to tissue located at the distal end of the catheter, a second optical fiber, removably insertable into one of the at least two lumens of the catheter shaft and extendable beyond the distal end of the catheter shaft, for conveying light back from the tissue for analysis by a spectroscopic diagnosis system, and an interventional device, wherein said first optical fiber and said second optical fiber are discrete fibers, and said interventional device is physically separable from said first and second optical fibers;

transmitting light through the first optical fiber to tissue located at the distal end of the catheter;

conveying light back from the tissue through the second optical fiber for analysis by a spectroscopic diagnosis system;

conveying light back from the tissue through at least one of the optical fibers for visual observation of the tissue;

diagnosing the tissue with the spectroscopic diagnosis system to determine whether an interventional procedure should be performed on the tissue; and engaging, with the interventional device, the tissue diagnosed by the spectroscopic diagnosis system in order to perform the interventional procedure on the tissue.

16. The method of claim 15, wherein the interventional procedure comprises marking the tissue by injecting a marking fluid into the tissue with the interventional device.

17. The method of claim 16, wherein the marking fluid is india ink.

18. The method of claim 16, further comprising the steps of:

withdrawing the catheter having the optical fibers and the interventional device; inserting into the body of the living being a second catheter having a second interventional device located at its distal end; and engaging, with the second interventional device of the second catheter, the tissue diagnosed by the spectroscopic diagnosis system in order to perform another interventional procedure on the tissue.

19. The method of claim 15, wherein the step of diagnosing the tissue using the spectroscopic diagnosis system comprises determining whether an interventional procedure should be performed on the tissue.

20. The method of claim 15, wherein the interventional procedure comprises removing tissue for biopsy analysis.

21. The method of claim 15, wherein the interventional procedure comprises removing tissue diagnosed by the spectroscopic diagnosis system as being unhealthy.

22. The method of claim 15, wherein the lumen comprises an alimentary lumen.

23. The method of claim 15, wherein the lumen comprises a pulmonary lumen.

24. The method of claim 15, wherein the step of diagnosing the tissue further comprises determining whether the tissue is a tumor.

25. The method of claim 24, wherein the step of diagnosing the tissue further comprises determining whether the tumor is cancerous.

26. The method of claim 15, further comprising the step of inserting through the lumen of the body of the living being an endoscope having a working channel, and wherein the step of inserting the catheter into the body of the living being comprises inserting the catheter into the working channel of the endoscope.

27. The method of claim 15, further comprising the step of conveying visualization light to the tissue through at least one of the optical fibers.

28. The method of claim 15, further comprising the step of conveying a fluid through the catheter shaft to the tissue usefull for enabling visual observation of the tissue.

29. The method of claim 15, further comprising the step of applying a vacuum to the tissue through the catheter shaft.

30. An assembly comprising:

an endoscope;

an enlongated catheter shaft defining at least two lumens and including a distal end, and constructed to be insertable through a working channel or the endoscope;

a first optical fiber, removably insertable into one of the at least two two lumens of the catheter shaft and extendable beyond the distal end of the catheter shaft, for transmitting light to tissue located at the distal end of the catheter shaft;

a second optical fiber, removably insertable into one of the at least two lumens of the catheter shaft and extendable beyond the distal end of the catheter shaft, for conveying light back from the tissue for analysis by a spectroscopic diagnosis system to determine whether an interventional procedure should be performed on the tissue, wherein said second optical fiber and said first optical fiber are discrete fibers and at least one of the fibers includes a viewing device for converting a second conveyed light back from the tissue into a visual observation image of the tissue; and an interventional device, constructed to be insertable through a working channel of an endoscope, for engaging tissue diagnosed by the spectroscopic diagnosis system in order to preform the interventional procedure on the tissue, wherein said interventional device is physically seperable from said first and second optical fibers.

31. The assembly of claim 30 wherein the interventional device is located at the distal end of the catheter shaft having the optical fibers.

32. A method of diagnosing and performing an interventional procedure on tissue, comprising the steps of:

inserting an endoscope through a lumen of a body of a living being;

inserting through a working channel of the endoscope a catheter having an elongated shaft defining at least two lumens and including a distal end, a first optical fiber, removably insertable into one of the at least two lumens of the catheter shaft and extendable beyond the distal end of the catheter shaft, for transmitting light to tissue located at the distal end of the catheter, a second optical fiber, removably insertable into one of the at least two lumens of the catheter shaft and extendable beyond the distal end of the catheter shaft, for conveying light back from the tissue for analysis by a spectroscopic diagnosis system wherein said first optical fiber and said second optical fiber are discrete fibers;

transmitting light through the first optical fiber to tissue located at the distal end of the catheter;

conveying light back from the tissue through the second optical fiber for analysis by a spectroscopic diagnosis system;

conveying light back from the tissue through at least one of the optical fibers for visual observation of the tissue;

diagnosing the tissue with the spectroscopic diagnosis system to determine whether an interventional procedure should be performed on the tissue; and engaging, with an interventional device insertable through a working channel of the endoscope, the tissue diagnosed by the spectroscopic diagnosis system in order to perform the interventional procedure on the tissue, wherein said interventional device is physically separable from said first and second optical fibers.

\* \* \* \* \*